(12) United States Patent
Cortelazzo (10) Patent No.: US 7,625,525 B2
(45) Date of Patent: Dec. 1, 2009

(54) MACHINE FOR PROCESSING SAMPLES OF BIOLOGICAL TISSUES AND THE LIKE

(75) Inventor: Lorenzo Cortelazzo, Padua (IT)

(73) Assignee: Kaltek S.R.L., Padua (IT)

( * ) Notice: Subject to any disclaimer, the term of this patent is extended or adjusted under 35 U.S.C. 154(b) by 634 days.

(21) Appl. No.: 11/271,882

(22) Filed: Nov. 14, 2005

(65) Prior Publication Data

US 2006/0110290 A1    May 25, 2006

(30) Foreign Application Priority Data

Nov. 23, 2004    (IT) .................... PD2004A000298

(51) Int. Cl.
*G01N 21/00* (2006.01)
*G01N 33/48* (2006.01)
*B01L 3/00* (2006.01)
*B01L 9/00* (2006.01)

(52) U.S. Cl. .................. 422/65; 422/63; 422/67; 422/68.1; 422/104; 436/43; 436/46; 436/47

(58) Field of Classification Search ................ 188/400, 188/423, 500; 422/63, 65, 67, 68.1, 99, 104; 436/43, 46, 47

See application file for complete search history.

(56) References Cited

U.S. PATENT DOCUMENTS

| | | | |
|---|---|---|---|
| 3,976,028 | A | 8/1976 | Howells et al. |
| 5,573,727 | A | 11/1996 | Keefe et al. |
| 6,444,170 | B1 | 9/2002 | Heid et al. |

FOREIGN PATENT DOCUMENTS

EP    0 884 577 A    12/1998

*Primary Examiner*—Jill Warden
*Assistant Examiner*—Dean Kwak
(74) *Attorney, Agent, or Firm*—Modiano & Associati; Albert Josif; Daniel J. O'Byrne (57) ABSTRACT

A machine for processing samples of biological tissues or the like, comprising a box-like structure, which delimits a compartment for accommodating trays for containing sample treatment liquid (the trays being arranged in preset positions of the compartment), and racks for supporting at least one sample supporting slide to be inserted in the trays. The machine comprises elements for transfer within the compartment for the trays and the racks, both individually and with the racks inserted in the trays.

19 Claims, 5 Drawing Sheets

MACHINE FOR PROCESSING SAMPLES OF BIOLOGICAL TISSUES AND THE LIKE

The present invention relates to a machine for processing samples of biological tissues and the like.

BACKGROUND OF THE INVENTION

Machines for processing samples of biological tissues in order to perform analyses on said samples, such as for example cytological analyses or histological analyses, are known.

One type of these machines, also known as stainers, comprises a box-like structure, which delimits internally a compartment for accommodating trays for containing the sample processing liquid.

Said trays are arranged in preset positions of the compartment and in practice are ordered according to a matrix-like structure.

Supporting ranks are associated with said trays and support a plurality of elements for supporting the samples to be processed, such as typically slides to which the portions of tissue to be processed and subsequently analyzed are applied.

The racks with the supporting elements are inserted in the trays in which the reagent liquids for processing the samples are present.

The racks with the samples are left there for a certain time (depending on the reaction required for processing) and are then removed, optionally dried and then taken out of the compartment.

The racks are generally moved by means of a transfer device with three axes, in practice the two directions of the matrix of the trays and the vertical direction.

A head for engaging the racks is provided on the transfer device.

A programmable electronic control unit is associated with the transfer device.

A typical operation of the machine arranges a rack loaded with slides in a loading region.

From here, according to a preset program, which depends on the type of processing and on the load that is already present in the machine, the transfer device, by means of the engagement head, picks up the rack from the loading region and transfers it into the preset tray, where the treatment will occur.

The rack is left there for a certain period, which depends on the process.

In the meantime, the engagement head can be moved in order to transfer other racks, both to insert them in the trays and to extract them and transfer them, after any other processes, to an unloading region.

After a certain time has elapsed, the engagement head returns at the preset tray and extracts the rack, moving it to the unloading region after any other processes.

For access to the compartment, there is a large door, which allows easy maneuvering to the operator during the step for arranging (or removing) the trays in the compartment, for example in order to replace or top up the processing liquid.

The reagents can release substances which are toxic or otherwise noxious for the operator.

It is therefore evident that opening the door and the activity inside the compartment can be harmful for said operator.

Further, during the manual transfer of the trays, the operator may cause dripping of the liquid of the trays that are being transferred downward, contaminating the liquids of the other trays deposited on the bottom of the compartment.

Automation of the handling of the racks entails considerable productivity in terms of processes per day with respect to manual handling techniques.

However, this productivity is limited by the fact that the trays with the reagent are loaded manually into the containment compartment and have to be extracted, again manually, from the compartment when the level or quality of the reagent has decreased below a threshold value.

The position of the trays is preset depending on the type of reagent that they use; it is therefore evident that in different positions it will be necessary to arrange trays with different reagents.

An operation for manual arrangement of the trays therefore requires particular care due to checking the correct placement of the trays.

This check further slows the daily productivity of the machine.

SUMMARY OF THE INVENTION

The aim of the present invention is to provide a machine for processing samples of biological tissues and the like which solves the problems related to known types.

Within this aim, an object of the present invention is to provide a machine for treating samples of biological tissues and the like which increases the safety for the operator assigned to the machine.

Another object of the present invention is to provide a machine for processing samples of biological tissues and the like which allows to avoid contamination by dripping of the trays arranged in the compartment during the step for transferring other trays.

Another object of the present invention is to provide a machine for processing samples of biological tissues and the like which allows to increase the degree of automation of the operations for loading and unloading the trays and the racks with respect to known machines.

Another object of the present invention is to provide a machine for processing samples of biological tissues and the like which can be manufactured with known systems and technologies.

This aim and these and other objects, which will become better apparent hereinafter, are achieved by a machine for processing samples of biological tissues or the like, of the type which comprises:

a box-like structure, which delimits a compartment for accommodating trays for containing sample treatment liquid, said trays being arranged in preset positions of said compartment, supporting racks for at least one sample supporting element to be inserted in said trays, characterized in that it comprises means for transfer within said compartment for said trays and said racks, both individually and with said racks inserted in said trays.

BRIEF DESCRIPTION OF THE DRAWINGS

Further characteristics and advantages of the invention will become better apparent from the following detailed description of a preferred but not exclusive embodiment thereof, illustrated by way of non-limiting example in the accompanying drawings, wherein.

DESCRIPTION OF THE PREFERRED EMBODIMENTS

With reference to the figures, a machine for processing samples of biological tissues or the like according to the invention is generally designated by the reference numeral 10.

The machine 10 comprises a box-like structure 11, which delimits internally a compartment 12 for accommodating trays 13 for containing the sample process liquid.

The trays 13 can be arranged in preset positions defined in the compartment 12, in practice in a matrix-like arrangement.

Figure 3:
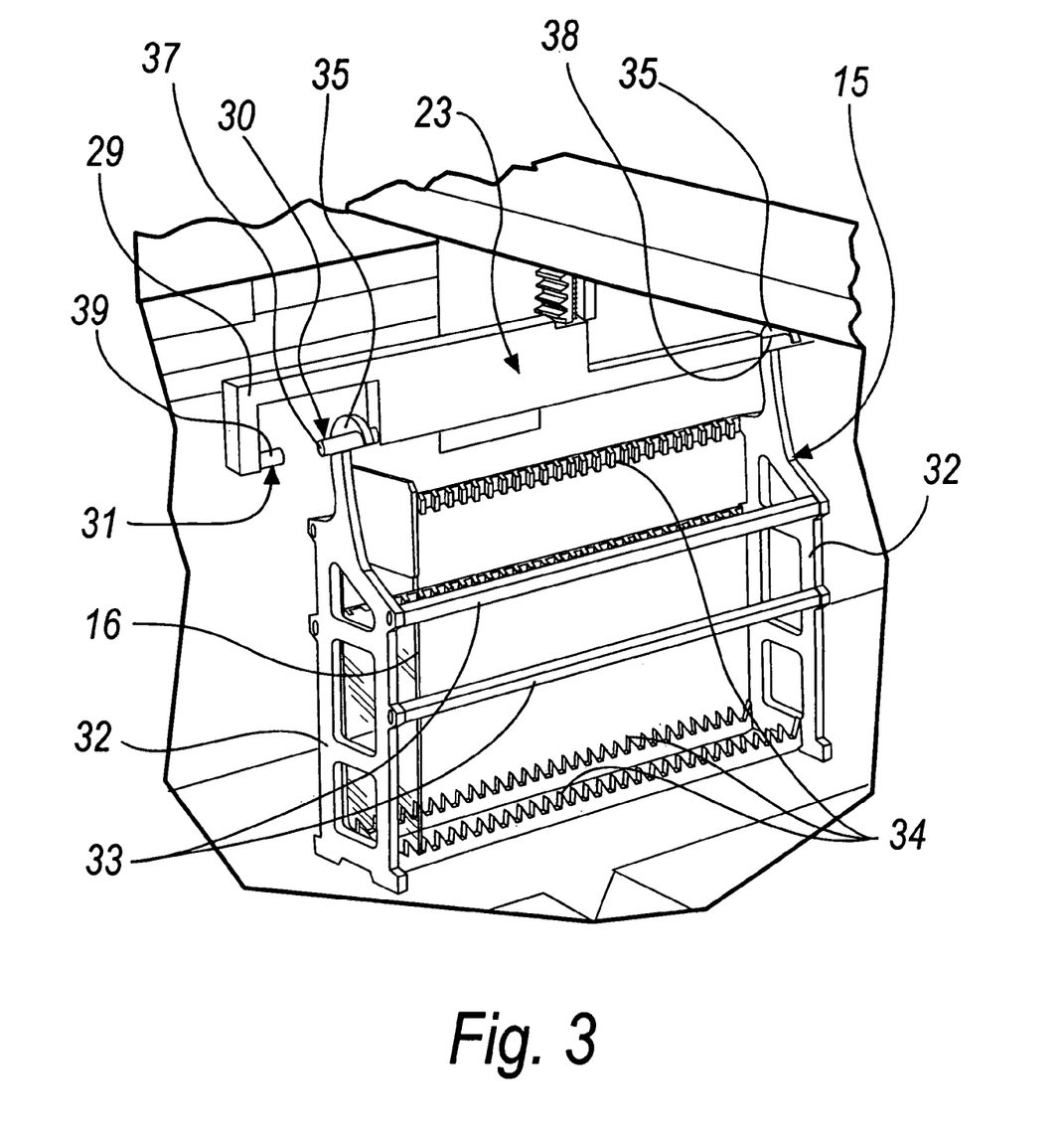
FIG. 3 is a perspective view of a supporting rack for elements for supporting slides, during transfer within the compartment of the machine of FIG. 1.

Racks 15 for supporting a plurality of supporting elements 16 for samples to be processed are associable with the trays 13 (only one element is shown in FIG. 3).

The supporting elements 16 are for example slides on which the samples to be processed are arranged.

The racks 15 are designed to be inserted in the trays 13 in order to perform the process on the samples, as will become better apparent hereinafter.

The machine 10 comprises means 17 for transfer within the compartment 12 for the trays 13 and the racks 15.

In particular, the transfer means 17 can handle individually a tray 13 or a rack 15 or, when the rack is inserted in a respective tray, move simultaneously, as if they were a single element, the tray 13 and the rack 15, as will become better apparent hereinafter.

The transfer means 17 comprise a transfer device with three axes, which is constituted by a motorized portal 18 arranged above the region for accommodating the trays 13 (the matrix).

The portal 18 can slide on guides 19 which are parallel to a main direction of the matrix-like arrangement of the trays 13.

A motorized slider 21 is arranged slidingly on the upper beam 20 of the portal 18.

Translational motion means 22 for the vertical translational motion of an engagement head 23 are associated with the slider 21.

The vertical translational means 22 are constituted for example by a vertical bar-rack 24, which is rigidly coupled to the engagement head 23 and meshes with a movement pinion 25, which is rotationally rigidly coupled on the slider 21.

The pinion 25 is keyed slidingly on a shaft 26, which has a transverse cross-section with a rotation-preventing contour, for example a square shape.

The shaft 26 is connected directly to an electric motor 27, which is arranged at the end of the upper beam 20 of the portal 18.

The motor for moving the slider 21 (not shown in the figures) is also arranged at the end of the upper beam 20 and is connected kinematically thereto by means of a toothed belt 28, which is closed in a loop and lies between two rotors (not shown in the figures), one of which is associated with the motor moving the slider 21, said rotors being arranged at the ends of the upper beam 20.

The slider 21 is fixed to a portion of the toothed belt 28.

First engagement means 30 for reversible engagement with the racks 15 and second engagement means 31 for reversible engagement with the trays 13, described in greater detail hereinafter, are associated with the engagement head 23.

Each rack 15 is constituted in practice by a frame which has two plate-like uprights 32 connected by cross-members 33 which form a cage in which suitable positioning abutments 34 are provided for the supporting elements 16 (slides) for the samples to be processed.

In this embodiment, the slides are oriented vertically and are parallel to each other.

Respective hook-shaped portions 35 protrude upward from the plate-like uprights 32.

Each tray 13 has, in this embodiment, a rectangular plan shape and is shaped so as to allow to accommodate a rack 15.

Figure 4A:
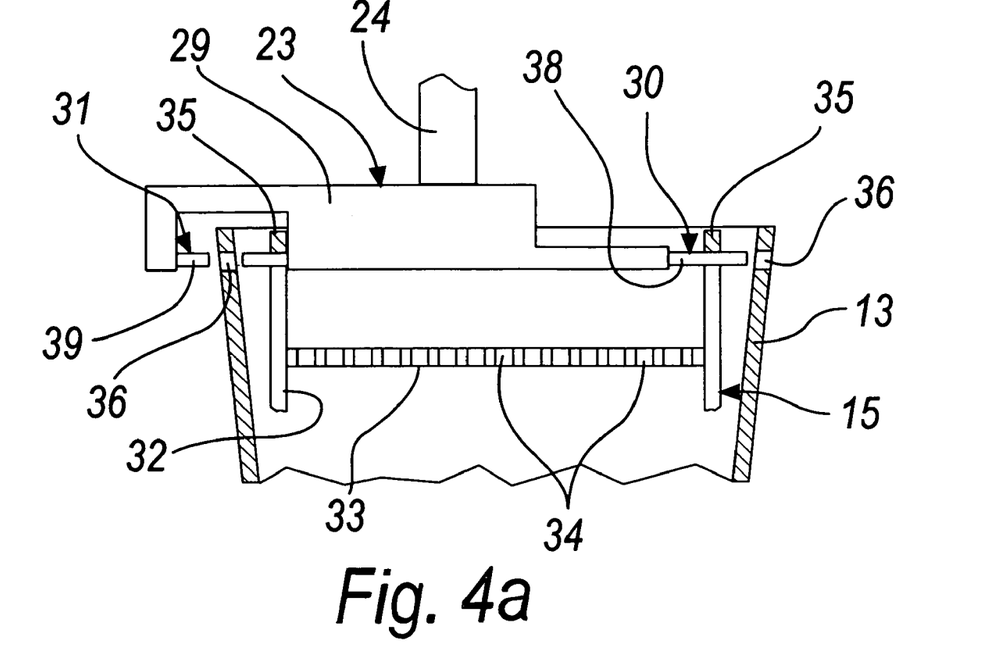
FIG. 4a is a partially sectional schematic view of a rack coupled to its transfer means and inserted in a corresponding tray containing processing liquid.
Figure 4B:
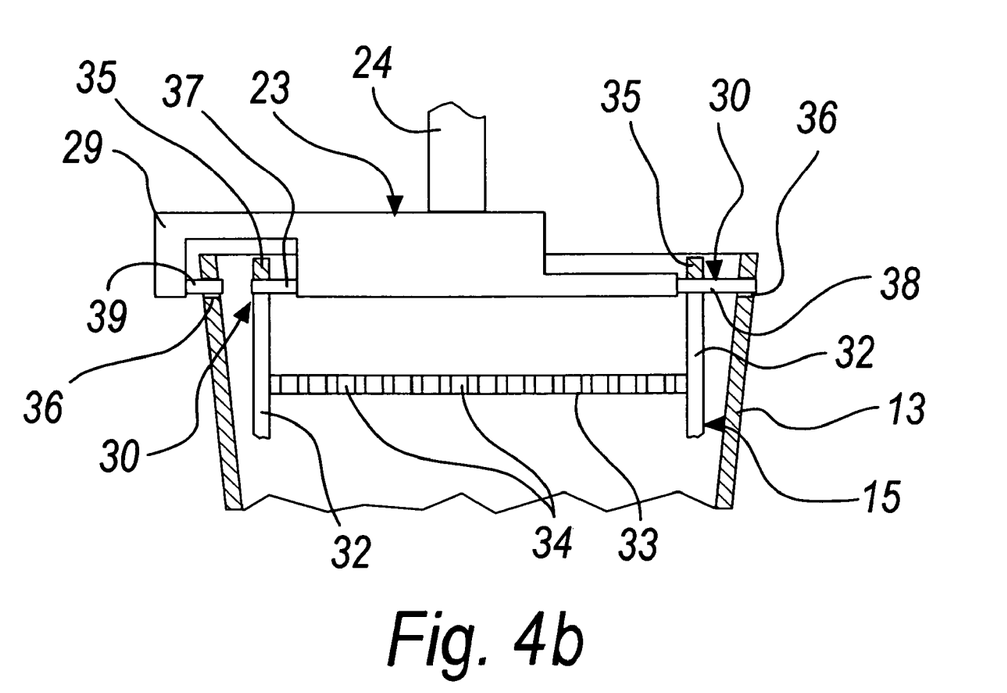
FIG. 4b is a partially sectional schematic view of the rack and of the tray of FIG. 4a, with the rack and the tray fastened to the transfer means.

When the rack 15 rests on the bottom of the tray 13, the hook-shaped portions 35 of said rack are contained within the tray 13 (as shown in FIGS. 4a and 4b) and do not protrude from the upper edge thereof.

On the short sides of the tray 13, at the plate-like uprights 32 from which the hook-shaped portions 35 protrude, there are respective engagement abutments 36, which are aligned with each other and with the axis of curvature of the hook-shaped portions 35 when the rack 15 rests on the bottom of the tray 13, as shown in FIGS. 4a and 4b.

The engagement abutments 36 are constituted by through holes, which are preferably polygonal (for example triangular).

The first means 30 for the reversible engagement of the engagement head 23 on the racks 15 are constituted for example by a first horizontal pin 37 and a second pin 38, which is also horizontal, said pins being mutually aligned and rigidly coupled to the engagement head 23 (see FIGS. 4a and 4b).

The corresponding hook-shaped portions 35 formed on the racks 15 are intended to be rested on said first and second pins 37 and 38.

The second reversible engagement means 31 are constituted for example by a third pin 39, which is rigidly coupled to the engagement head 23 and is aligned with the first and second pins 37 and 38.

The third pin 39 protrudes from the free end of an inverted L-shaped portion 29 which protrudes from the engagement head 23.

The free ends of the third pin 39 and of the first pin 37 are aligned and mutually spaced at the front.

The respective engagement abutments 36 of the tray 13 can be arranged so as to rest on the third pin 39 and on the second pin 38.

The pins 37, 38 and 39, as well as the engagement abutments 36 and the axis of curvature of the hook-shaped portions 35, are parallel to one of the main directions of the positioning matrix of the trays 13 and are therefore parallel to one of the two horizontal directions of movement of the engagement head 23.

The third pin 39 and the end part of the second pin 38 are shaped complementarily with respect to the engagement abutments 36 in order to avoid oscillations during the transfer of the tray 13.

Figure 5:
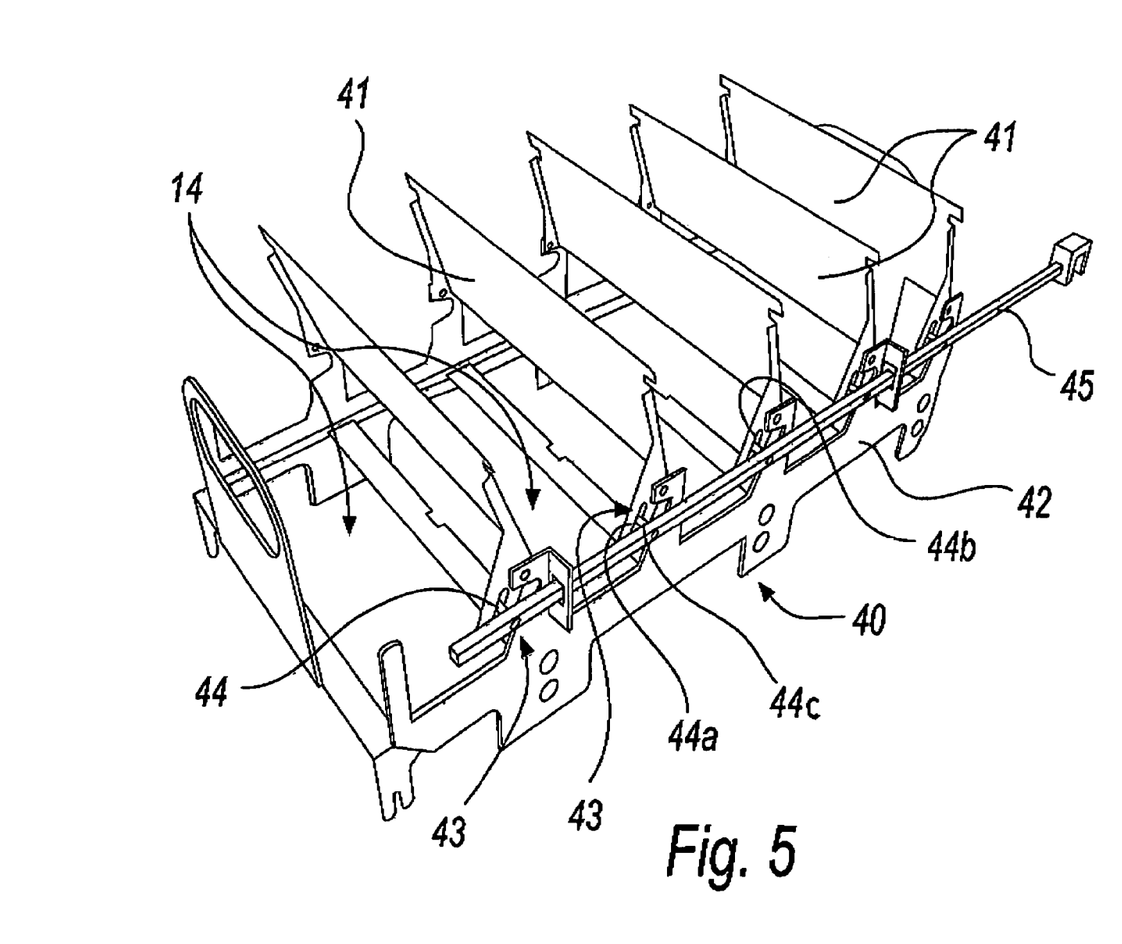
FIG. 5 is a perspective view of a frame for supporting the trays in the containment compartment of the machine of FIG. 1, with which covering means for said trays are associated.

Covering means 40 are associated with the trays 13 arranged in the compartment 12 and are constituted by lids 41, which are pivoted to a supporting frame 42.

The supporting frame 42 delimits the tray compartment 14 for accommodating each tray 13.

In particular, there is a supporting frame 42 for each column (or row) of trays 13 provided in the compartment 12.

Opening and closing means 43 are associated with the lids 41 and are constituted by a plurality of linear cams 44, which are formed proximate to the points where the lids 41 are pivoted to the supporting frame 42.

The linear cams 44, once moved, cooperate with the lids 41, allowing their rotation about their own pivoting axis.

The linear cams 44 are all moved simultaneously by way of an actuation arm 45, which is connected to a translational actuator, not shown in the figures; an actuation arm 45 is provided for each supporting frame 32.

In particular, the linear cams 44 are constituted by a portion 44a of each lid 41 which is eccentric with respect to its pivoting axis and on which there is an inclined track 44b, inside which there is a pin-shaped slider 44c, which is rigidly coupled at right angles to the actuation arm 45 parallel to the pivoting axes of the lids 41.

The box-like structure 11 has three doors for accessing the compartment 12.

Figure 1:
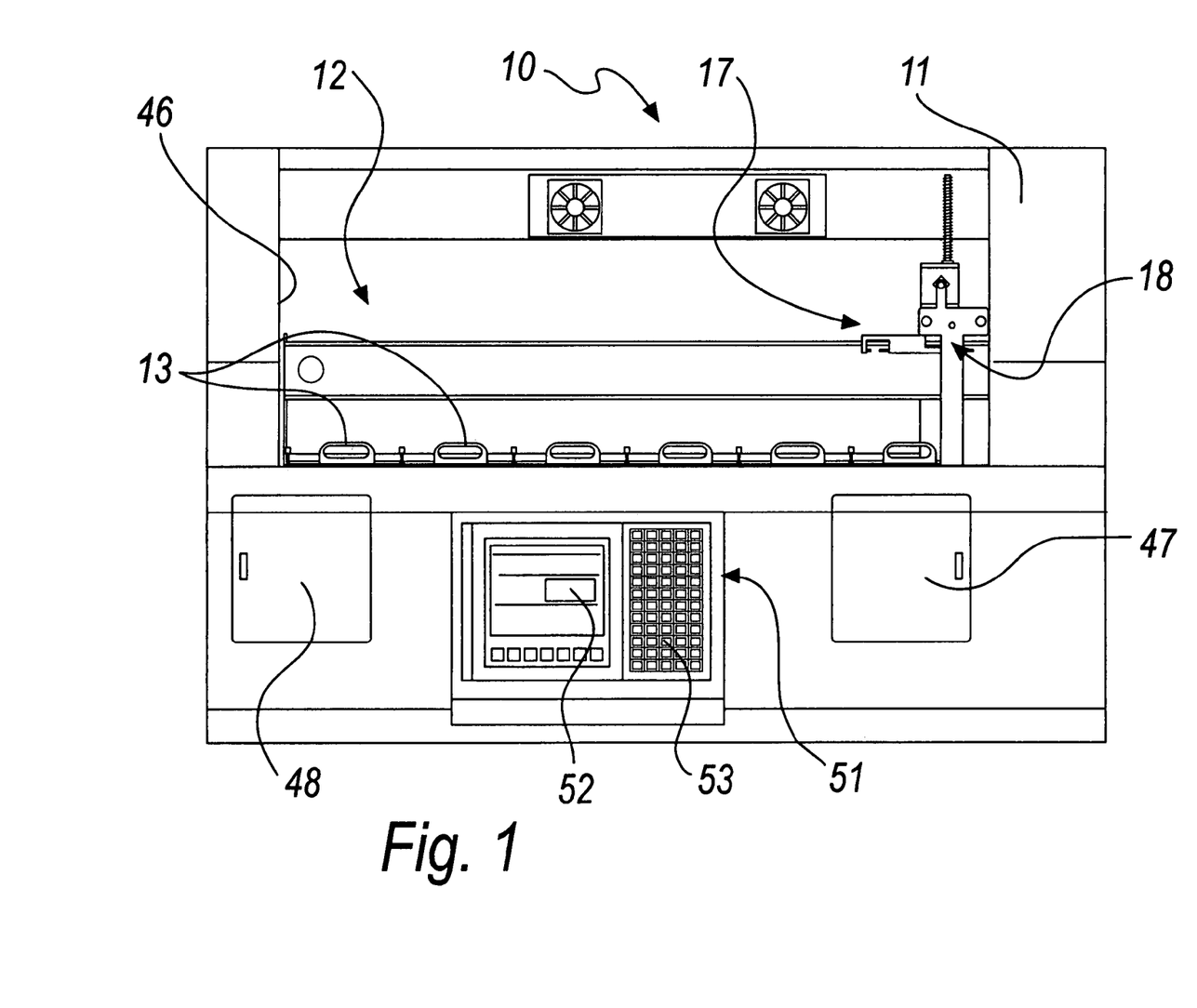
FIG. 1 is a front perspective view of a machine according to the invention.
Figure 2:
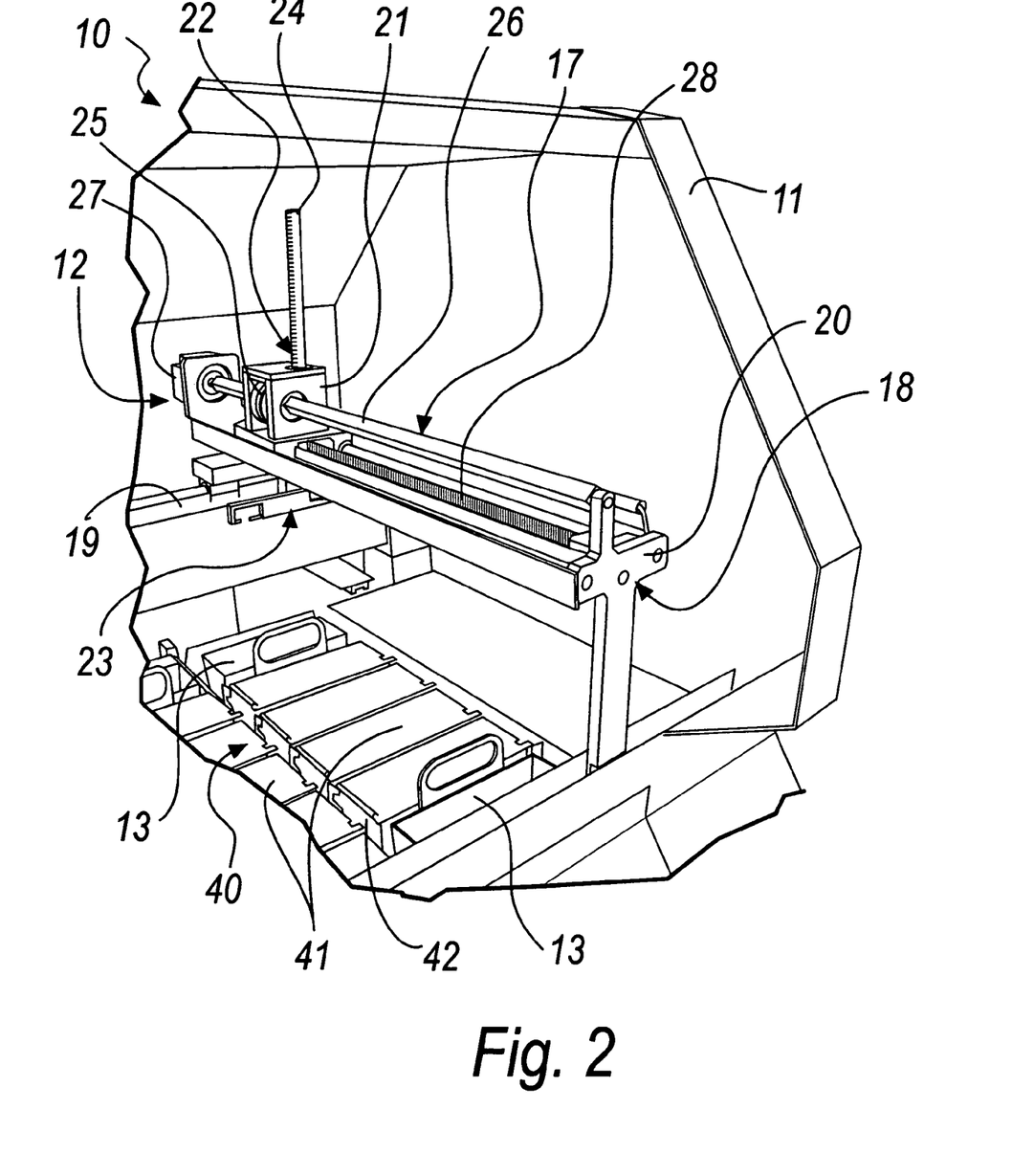
FIG. 2 is a perspective view of a portion of the internal compartment of the machine of FIG. 1.

In particular, it has a first door 46 (only the perimeter of which is shown in FIG. 1), which has dimensions substantially comparable to the width of the compartment 12 and is arranged centrally, allowing easy and convenient access to the compartment 12.

Below the first door 46, in two mutually opposite lateral positions, there is a second door 47, for loading the racks 15, and there is a third door 48, for loading the trays 13.

Respective drawers (not shown in the figures) onto which a plurality of racks 15 and of trays 13 are to be placed are associated with the second and third doors 47 and 48.

Said drawers allowed to move the racks 15 and the trays 13 from the outside to the inside of the compartment 12 (and vice versa).

A programmable electronic unit 51 for controlling the machine is arranged between the second door 47 and the third door 48 and manages the movements of the engagement head 23 according to the set programs.

A display 52 and a keyboard 53 are associated with the electronic unit 51.

The operation of the invention is as follows.

Assume it is necessary to immerse a rack 15 in a given tray 13 within the compartment 12.

The rack 15 is deposited on the drawer at the second door 47.

The drawer is moved into the compartment 12 and the second door 47 is closed.

The engagement head 23 is moved to the region where the rack 15 is located.

At this point, said head is moved downward until the first and second pivots 37 and 38 are arranged laterally and below the hook-shaped portions 35.

A lateral movement of the engagement head 23 causes said first and second pivots 37 and 38 to be arranged "within" the hook-shaped portions 35.

When the engagement head 23 is moved upward, the rack 15 follows it, as it hangs therefrom.

The engagement head is moved above the corresponding tray 13 in which it is to be immersed.

The lids 41 related to the supporting frame 40 of the column in which the corresponding tray 13 is arranged are opened by acting on the actuation arm 45, which moves the linear cams 44 connected to said lids.

The engagement head 23 moves downward until the rack 15 lies within the tray 13 and is left there for a certain period of time.

Once the reaction time has ended, the engagement head is disengaged from the tray and the rack is moved to other processing stations (for example drying stations) and is then placed at the drawer that relates to the door from which it is to be removed.

If it is necessary to move simultaneously the tray and the rack inserted therein, the engagement head 23 can engage the tray 13 simultaneously with the rack 15.

When the rack is inserted in the tray 13 and is engaged with the engagement head 23, the horizontal translational motion of said engagement head toward the engagement pins in fact allows to move the third pin 39 and the second pin 38 on the engagement abutments 36 (triangular holes) of the tray, at the same time maintaining the engagement on the rack 15.

Therefore, it is possible to lift the tray 13 and the rack 15 as a single unit (both hang from the engagement head 23) and move them according to the requirements.

It is evident that it is also possible to move just the trays, for example to load or unload the compartment 12.

During the transfer of the rack or tray (or both) in the compartment 12, the lids 41 are closed, in order to prevent any dripping from contaminating the other trays that are present in the same compartment 12.

It is evident that it is possible to program the machine so that it optimizes work times, for example by moving other racks or trays during the processing periods of one series of samples inserted in corresponding trays.

In practice it has been found that the invention thus described solves the problems noted in known types of machine for processing samples of biological tissues.

In particular, the present invention provides a machine for processing samples of biological tissues or the like which allows to increase safety for the assigned operator, since the provision of an engagement head which can engage the trays allows to perform operations for loading and unloading them, without having to do this work manually and therefore avoiding the need to open the first door.

Further, this automation of the handling of the trays reduces considerably the risk of dripping during their handling.

The risk is reduced further also by way of the tray covering means.

Further, the increase in the degree of automation of operations leads to an increase in daily productivity.

The provision of an engagement head which can engage the trays in fact allows to perform operations for loading and unloading them without having to do this work manually.

In this manner, the time due to the checking of the correct placement of the trays within the compartment is also reduced (since placement occurs automatically according to a programmed cycle), thus reducing the risks of error.

Moreover, the fact of being able to engage simultaneously both the tray and the rack aroused allows to move them both together outside the compartment (if necessary), thus reducing the time related to unloading performed separately and sequentially.

The invention thus conceived is susceptible of numerous modifications and variations, all of which are within the scope of the appended claims; all the details may further be replaced with other technically equivalent elements.

In practice, the materials employed, so long as they are compatible with the specific use, as well as the dimensions, may be any according to the requirements and the state of the art.

The disclosures in Italian Patent Application No. PD2004A000298 from which this application claims priority are incorporated herein by reference.

What is claimed is:

1. A machine for processing samples of biological tissues, comprising:

a box-like structure, which delimits a compartment;

trays accommodated in said compartment for containing sample treatment liquid, said trays being provided with engagement abutments and being arranged in preset positions of said compartment so as to be transferrable with vertical, lifting and horizontal, translational motions;

supporting racks for at least one sample supporting element to be inserted in said trays;

transfer means for transferring within said compartment said trays and said racks, both individually and with said racks inserted in said trays by said vertical, lifting and horizontal, translational motions; and wherein said transfer means comprise; an engagement head, rigidly coupled to a three-axis handling device; first engagement means for reversible engagement with said racks; and second engagement means for reversible engagement with said engagement abutments of said trays, said first and second engagement means being associated with said engagement head and being suitable move said trays and racks, both individually and with said racks inserted in said trays, to perform said vertical, lifting and horizontal, translational motions.

2. The machine of claim 1, wherein said first reversible engagement means comprise: at least one first pin and at least one second pin, both of which are horizontally parallel and rigidly coupled to said engagement head; and corresponding hook-shaped portions formed on each one of said racks that are rested on said at least one first and second pins.

3. The machine of claim 2, wherein said second reversible engagement means comprise: at least one third pin, which is rigidly coupled to said engagement head and is parallel to said at least one first and second pins, with free ends of said at least one third pin and of said at least one first pin being spaced at front parts thereof; and wherein said engagement abutments of said tray are arrangeable so as to rest on said at least one third pin and said at least one second pin, a horizontal translational motion of said engagement head with a rack inserted in a corresponding tray being suitable to move into position said at least one third pin and said at least one second pin on said engagement abutments of said tray, while maintaining engagement on said rack.

4. The machine of claim 3, wherein said engagement head is movable along two horizontal directions, said at least one first, second and third pins being mutually aligned and parallel to one of the two horizontal directions of motion of said engagement heat.

5. The machine of claim 4, having an inverted L-shaped portion which protrudes from said engagement head, said at least one third pin protruding from a free end of said inverted L-shaped portion.

6. The machine of claim 4, wherein said trays are arrangeable in preset positions defined in said compartment in a matrix arrangement, said engagement head being movable vertically and along main directions of said matrix arrangement.

7. The machine of claim 6, comprising: guides which are parallel to a main direction of the matrix arrangement of said trays, said three-axis handling device being constituted by a motorized portal, which lies above a region for accommodating said trays, said portal being able to slide on said guides; a motorized slider arranged slidingly on an upper beam of said portal; and translational motion means for vertical translational motion of said engagement head associated with said slider.

8. The machine of claim 7, comprising: an electric motor which is arranged at an end of said upper beam of said portal; a shaft which has a rotation-preventing transverse cross-section, said shaft being connected directly to said electric motor; and a movement pinion which is rigidly rotationally coupled on said slider, said pinion being keyed slidingly on said shaft, said vertical translational motion means being constituted by a vertical rack-bar, which is rigidly coupled to said engagement head and meshes with the movement pinion, said slider being provided with an actuation motor also arranged at said end of said upper beam, connected kinematically to said upper beam and with two rotors and with a toothed belt which is closed in a loop and lies between the two rotors, one of which is associated with the motor for actuating the slider, said rotors being arranged at ends of said upper beam, said slider being further fixed to a portion of said toothed belt.

9. The machine of claim 3, wherein each one of said racks is constituted by a frame which is provided with two plate-shaped uprights, which are connected by cross-members, forming a cage in which preset positioning abutments are provided for said at least one sample supporting element for supporting the samples to be processed, said corresponding hook-shaped portions protruding upward from said plate-shaped uprights.

10. The machine of claim 9, wherein each tray has a rectangular plan shape and is shaped so as to allow the accommodation of a said rack, said engagement abutments being constituted by polygonal through holes, said third pin and an end part of said second pin being shaped complementarily with respect to said engagement abutments.

11. The machine of claim 10, comprising covering means that are associated with said trays arranged in said compartment.

12. The machine of claim 11, wherein said covering means are constituted by lids, which are pivoted to at least one supporting frame, by opening means for opening and closure that are associated with said lids and are constituted by a plurality of linear cams formed proximate to points about which said lids are pivoted to said supporting frame and being actuatable by way of a translational actuator, said linear cams, once moved, being adapted to cooperate with said lids, for allowing rotation thereof about a pivoting axis thereof.

13. The machine of claim 12, comprising a said supporting frame for each column or row of said trays provided in said compartment.

14. The machine of claim 13, wherein said linear cams of a said frame are provided so as to all cooperate simultaneously with an actuation arm connected to a translational actuator.

15. The machine of claim 14, wherein said linear cams are constituted by a portion of each one of said lids which is eccentric with respect to the pivoting axis thereof and on which an inclined track with inside a pin-shaped slider is provided, which is rigidly coupled at right angles to said actuation arm so as to be parallel to the pivoting axes of said lids.

16. The machine of claim 15, wherein said at least one supporting frame delimits said compartment for said trays.

17. The machine of claim 11, wherein said box-like structure has a first door, which is arranged centrally and has dimensions which are comparable substantially to a width of said compartment, wherein below said first door, in two mutually opposite lateral positions, a second door for loading said racks and a third door for loading said trays are provided, and wherein respective drawers on which at least one said rack and at least one said tray are to be arranged are associated with said second and third doors.

18. The machine of claim 17, further comprising: a programmable electronic unit for controlling the machine, which manages movements of said engagement head according to the set programs; and a display and a keyboard that are associated with said electronic unit.

19. A machine for processing samples of biological tissues, comprising:

a box-like structure, which delimits a compartment;

trays accommodated in said compartment for containing sample treatment liquid, said trays being arranged in preset positions of said compartment;

supporting racks for at least one sample supporting element to be inserted in said trays;

transfer means for transferring within said compartment said trays and said racks, both individually and with said racks inserted in said trays;

wherein said transfer means comprise: an engagement head, rigidly coupled to a three-axis handling device; first engagement means for reversible engagement with said racks; and second engagement means for reversible engagement with said trays, said first and second engagement means being associated with said engagement head; and wherein said first reversible engagement means comprise: at least one first pin and at least one second pin, both of which are horizontally parallel and rigidly coupled to said engagement head; and corresponding hook-shaped portions formed on each one of said racks that are rested on said at least one first and second pins.

* * * * *